(12) United States Patent
Alberte et al.

(10) Patent No.: US 7,108,861 B1
(45) Date of Patent: *Sep. 19, 2006

(54) ENVIRONMENTALLY BENIGN CROP PROTECTION AGENTS

(75) Inventors: Randall S. Alberte, Falmouth, ME (US); Richard C. Zimmerman, Pacific Grove, CA (US)

(73) Assignee: Cernofina, LLC, Fort Meyers, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/405,299

(22) Filed: Sep. 23, 1999

Related U.S. Application Data

(63) Continuation-in-part of application No. 09/159,814, filed on Sep. 23, 1998, now abandoned.

(51) Int. Cl.
*A01N 25/28* (2006.01)
*A01N 31/00* (2006.01)
*A01N 41/02* (2006.01)
*A01P 1/00* (2006.01)
*A01P 3/00* (2006.01)

(52) U.S. Cl. ...................... 424/405; 424/408; 424/417; 424/457; 424/459; 424/490; 428/402; 428/402.2; 428/402.24; 428/907; 427/4; 47/DIG. 11

(58) Field of Classification Search ............... 424/93.7, 424/405; 428/411.1, 704, 543, 907; 427/4; 47/57.6, DIG. 11; 504/100; 558/20, 37, 558/38

See application file for complete search history.

(56) References Cited

U.S. PATENT DOCUMENTS

| | | | | |
|---|---|---|---|---|
| 2,190,733 | A | * | 2/1940 | Richmond .................... 558/37 |
| 3,133,949 | A | * | 5/1964 | Rutkowski et al. ............ 558/36 |
| 4,046,731 | A | | 9/1977 | Mortimer et al. |
| 4,053,610 | A | * | 10/1977 | Walworth |
| 4,087,597 | A | * | 5/1978 | Häfeli |
| 4,243,549 | A | * | 1/1981 | Messenger et al. ............ 516/25 |
| 4,281,110 | A | | 7/1981 | Blount |
| 5,057,533 | A | * | 10/1991 | Tanaka et al. ................ 514/396 |
| 5,066,706 | A | | 11/1991 | Destryker et al. |
| 5,384,176 | A | * | 1/1995 | Zimmerman et al. .......... 428/68 |
| 5,607,741 | A | * | 3/1997 | Zimmerman et al. .......... 428/68 |

FOREIGN PATENT DOCUMENTS

| | | |
|---|---|---|
| DE | 32 29 097 A1 | 2/1984 |
| FR | 1. 696 M | 2/1963 |
| JP | 04279531 | 10/1992 |

OTHER PUBLICATIONS

The Merck Index, Tenth Ed., pp. 876-877, Merck & Co., Inc., Rahway, N.J., U.S.A. (1983).*
Afinogenov and Panarin; "Alkyl Sulfates and Alkylarylsulfonates as Penicillinase Inhibitors", Antibiotiki (Moscow) 21(10): 876-880 (1976)(Abstract), no month.
Anan'eva et al.; "Effect of Surfactants on Staphylococcal Plasmocoagulase", Zh. Mikrobiol. Epidemiol. Immunobiol., 6: 111-115 (1977) (Abstract), no month.
Elinov and Afinogenov ; "Effect of Sulfonol and Alkyl Sulfate on Penicillin Resistant Staphylococci Separated from Bone Wounds", Tr. Leningrad. Khim.-Farm. Inst., 27: 64-72 (1969) (Abstract No. 20F835), no month.
Panarin et al.; "Mechanism of Penicillinase Inhibition by Alkyl Sulfates in the Presence of Synthetic Polyelectrolytes", Antibiotiki (Moscow) 22(6): 502-506 (1977) (Abstract), no month.
Panarin and Afinogenov; "Relation Between Structure and Antimicrobial Activity in Alkyl Sulfates", Khim. Farm. Zh. 12(1); 79-81 (1978) (Abstract), no month.
Todd et al.; "The Antifouling Activity of Natural and Synthetic Phenolic Acid Sulphate Esters", Phytochemistry 34(2): 401-404 (1993), no month.

* cited by examiner

*Primary Examiner*—Marie Yamnitzky
(74) *Attorney, Agent, or Firm*—Foley Hoag LLP

(57) ABSTRACT

Disclosed are environmentally benign crop protection compounds that interfere with the attachment of a broad range of plant pathogens to plant cells surfaces.

6 Claims, 10 Drawing Sheets

ENVIRONMENTALLY BENIGN CROP PROTECTION AGENTS

RELATED APPLICATIONS

This application is a continuation-in-part of U.S. patent application Ser. No. 09/159,814, filed Sep. 23, 1998, now abandoned.

BACKGROUND OF THE INVENTION

There are more than 50,000 species of fungi. Fewer than 100 are pathogenic to humans. However, more than 10,000 fungi cause disease in plants. Fungal pathogens are extremely costly pests, affecting a broad range of crop plants. It is estimated that anywhere between 20–30% of crop production is lost to fungal pathogens alone worldwide with the greatest losses outside the United States (FAO Report). Losses from fungal pathogens are realized in every stage of crop production ranging from those fungi that attack seeds or germinating seed to those that attack the stems of seedlings, the roots, stems, vascular system, fruits and leaves of mature crops.

There are presently a number of widely used fungicide products on the market, including triazoles, anilides, dithiocarbamates, and benzimidazoles. Total worldwide sales of fungicides in 1995 approached $60 billion with greater than 80% of the market being non-U.S.

Essentially all of the non-biological fungicides are toxic chemicals to the fungi, as well as to the environment when they enter drinking water supplies and natural waters and can be toxic to animals and humans through accidental contact. In addition, many of the chemicals generate resistance in the target organisms.

Biological control is based on inhibition by some microorganisms on the growth and action of pathogenic fungi, which cause rotting (See for example, U.S. Pat. No. 4,975,277 and EP 0 781 843 A1). However, there can be great variations in the antifungic activity of different isolates or strains of the same species. In addition, the effectiveness of various strains may be diminished during storage and harvesting.

SUMMARY OF THE INVENTION

In one aspect, the instant invention features crop protection compounds having the general structure 1:

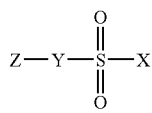

wherein

X represents —OH, —O(aryl), —O(acyl), —O(sulfonyl), —CN, F, Cl, or Br;

Y represents O, S, Se, or NR;

Z represents optionally substituted alkyl, heteroalkyl, cycloalkyl, heterocycloalkyl, aryl, heteroaryl, aralkyl, heteroaralkyl, or —(CH$_2$)$_m$—Rso;

R represents independently for each occurrence hydrogen, alkyl, heteroalkyl, aryl, heteroaryl, aralkyl, heteroaralkyl, or —(CH$_2$)$_m$—Rso;

R$_{80}$ represents independently for each occurrence aryl, cycloalkyl, cycloalkenyl, heterocyclyl, or polycyclyl; and m is an integer in the range 0 to 8 inclusive. Other preferred compounds are salts of the compounds in structure 1.

The instant claimed compounds interfere with the attachment of organisms to surfaces, thereby having broad applicability in effectively inhibiting the attachment of a variety of organisms. In addition, the compounds are relatively safe for wide-spread environmental use, as they naturally degrade into carbon dioxide and water, or simple organic acids.

In addition, certain preferred compounds have a relatively short half-life after release, rendering them particularly well-suited for widespread environmental use. Yet other preferred compounds can be readily synthesized.

Particularly preferred compounds include: p-iso-butylphenyl chlorosulfate, p-tert-butylphenyl chlorosulfate, p-tert-amylphenyl chlorosulfate, p-tert-cumylphenyl chlorosulfate, 4-pentylphenyl chlorosulfate, 4-(1-methylheptyl) phenyl chlorosulfate, methyl chlorosulfate, octyl chlorosulfate, bisphenyl diacid sulfate, p-iso-butylphenyl sulfate, p-tert-butylphenyl sulfate, p-tert-amylphenyl sulfate, p-tert-cumylphenyl sulfate, 4-pentylphenyl sulfate, 4-(1-methylheptyl)phenyl sulfate, methyl sulfate, and octyl sulfate, p-sulfoxy cinnamic acid, p-sulfoxy ferulic acid, m,p-disulfoxy caffeic acid, benzoic acid sulfate, vanillic acid sulfate, gentissic acid sulfate, gallic acid sulfate, protochateuic acid and zosteric acid and salts thereof.

Other features and advantages of the invention will be apparent from the following detailed description and claims.

DETAILED DESCRIPTION OF THE INVENTION

General

Figure 1:
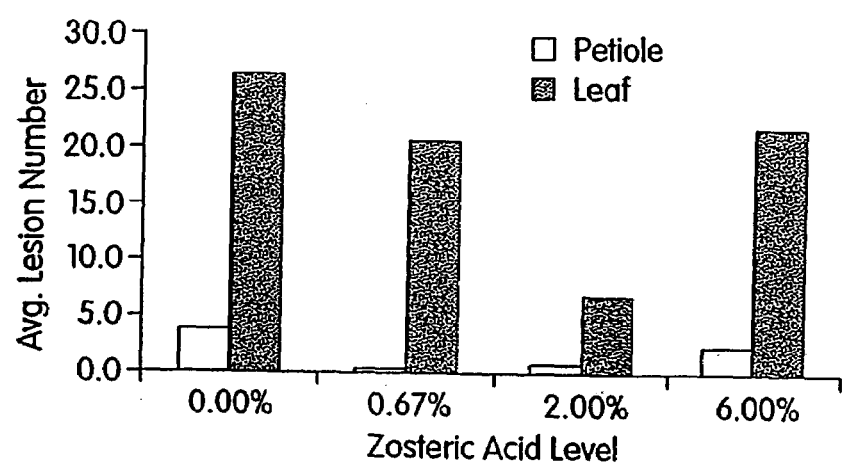
FIG. 1 is a bar graph plotting the average number of anthracnose lesions on the leaf and petioles of detached Chandler strawberries when treated with a range of concentrations of the sodium salt of zosteric acid. Anthracnose disease control efficacy of 73.6% was achieved with a 2% (w/v) solution of zosteric acid in phosphate buffer containing 0/1% Tween™ 20. *Colletotrichum fragariae* isolate CF63conidia (1.5×10$^6$ spores/mL) were used to induce disease.
Figure 2:
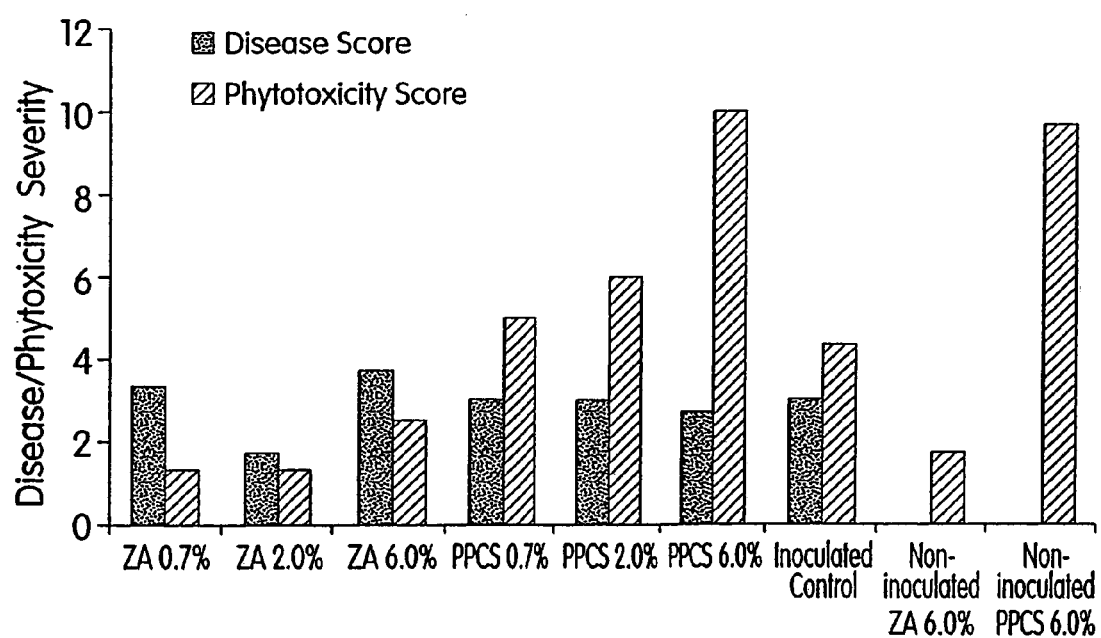
FIG. 2 is a graph showing the average disease severity and phytotoxicity ratings of Chandler strawberry whole plants when treated with a range of concentrations of the sodium salt of zosteric acid and an analog. *Colletotrichum fragariae* isolates CF63conidia (1.5×10$^6$ spores/mL) were used to induce disease.
Figure 3:
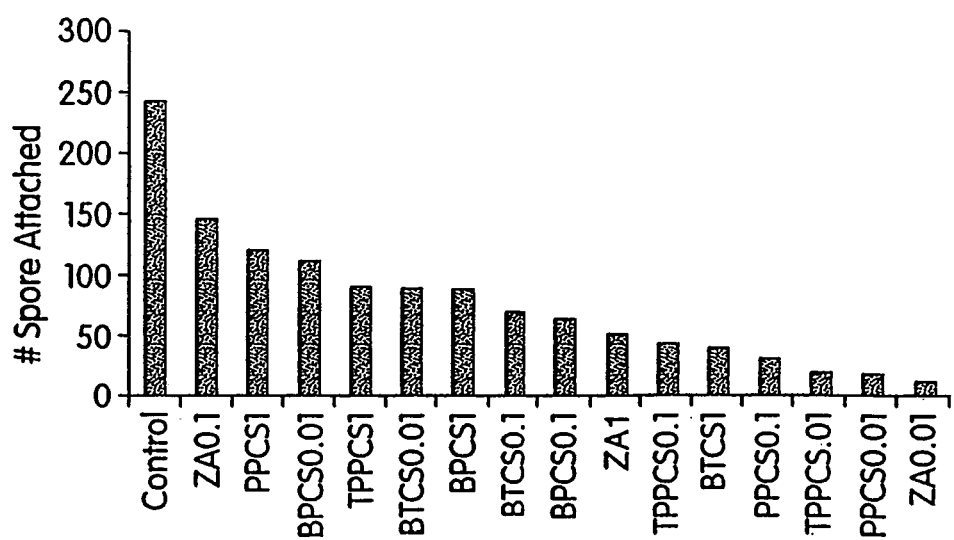
FIG. 3 is a graph showing the result of microscopic studies indicate that the sodium salt of zosteric acid and its TPPC analog were the most effective compounds at inhibiting spore attachment (*C. acutatum*) to a glass surface.

The instant invention is based, at least in part, on the finding described in detail in the following Example 1, that compounds of the invention inhibit attachment of parasitic fungi spores to plants, as well as hyphal production from previously attached spores. Even after prolonged exposure, the presence of the compounds of the invention on the plants did not result in any toxic or growth inhibitory effect.

In addition, greenhouse studies revealed that the compound effectively controlled the disease on plants exposure to abnormal high spore pressures. Again, no detectable phytotoxicity was observed. In evaluations assessing fungal spore attachment on man-made surfaces, it was determined that a compound of the invention provided nearly 100% inhibition of attachment of two species of fungal pathogens. If fungal spores were allowed to attach, the compound provided 100% inhibition of spore germination.

By blocking spore attachment, an initial step in the infection process, the compounds of the invention provide a highly effective antifungal agent. In addition, since essentially all fungal plant pathogens use spores to recognize the host plant, attach, germinate, penetrate the host plant tissue and proliferate hyphae that allows the fungus access to the plant's nutrients for growth and reproduction, the compounds are broad-based antifungal agents. In addition a series of investigations on several species of bacteria, microalgae, macroalgal spores and invertebrates has confirmed that the inhibitory mode-of-action is through a non-toxic means (Zimmerman et al., (1995) U.S. Pat. No. 5,384,176; Zimmerman et al., (1997) U.S. Pat. No. 5,607,741; Todd et al., *Phytochemistry* 34: 401–404 (1993); Sundberg et al., *Naval Research Reviews* (1997) 4: 51–59).

Although the exact mechanism of action is not known, studies indicate that the mechanism involves binding of the compounds to a sulfate binding moiety on cells. The compound or a functional fragment thereof, must then be released for the inhibitory effect. If permanently tethered to a surface, the compounds and sulfate groups tend to promote rather than inhibit the attachment and growth of organisms on a surface.

DEFINITIONS

For convenience, certain terms employed in the specification, examples, and appended claims are described below.

The term "acylamino" is art-recognized and includes a moiety that may be represented by the general formula:

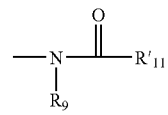

wherein $R_9$ is as defined below, and $R'_{11}$ represents a hydrogen, an alkyl, an alkenyl or —$(CH_2)_m$—$R_8$, where m and $R_8$ are as defined below.

The terms "alkenyl" and "alkynyl" are art-recognized, and include unsaturated aliphatic groups analogous in length and possible substitution to the alkyls described below, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described below.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., —$C_1$–$C_{30}$ for straight chain, $C_3$–$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term alkyl is includes —$CF_3$.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined below. Representative alkylthio groups include methylthio, ethyl thio, and the like.

The term "amido" is art recognized as an amino-substituted carbonyl and includes a moiety that can be represented by the general formula:

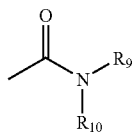

wherein $R_9$, $R_{10}$ are as defined below. Preferred embodiments of the amide will not include imides which may be unstable.

The terms "amine" and "amino" are art recognized and refer to both unsubstituted and substituted amines, e.g., a moiety that can be represented by the general formula:

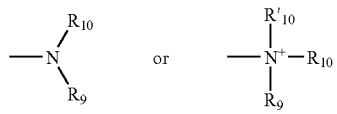

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art recognized and includes such moieties as can be represented by the general formula:

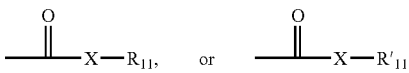

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

A "coating" refers to any temporary, semipermanent or permanent layer or covering. A coating can be a gas, vapor, liquid, paste, semi-solid or solid. In addition a coating can be applied as a liquid and solidify into a hard coating. Examples of coatings include sprays, liquids, gases, vapors, gels, powders, waters, wetters, detergents, oils.

"Contacting" as used herein refers to any means for providing the compounds of the invention to a plant of plant component. Contacting can include spraying, wetting, immersing, dipping, painting, bonding, adhering or otherwise providing a surface with a compound of the invention.

The phrase "effective amount" refers to an amount of the disclosed antifouling compounds that reduces the number of organisms that attach to a defined surface (cells/mm$^2$) of a plant or plant component relative to the number that attach to an untreated surface. Particularly preferred are amounts that reduce the number of organisms that attach to the surface by a factor of at least 2. Even more preferred are amounts that reduce the surface attachment of organisms by a factor of 4, more preferably by a factor of 6, 8, 10 or more. Especially preferred is that amount, which will completely inhibit fungal growth (i.e. inhibit the spread of fungal mycelia) without causing necrotic tissue to the plant.

The phrase "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "half-life" refers to the amount of time required for half of a compound to be eliminated or degraded by natural processes. Preferred compounds have a half-life of less than one year. Particularly preferred are half-lives in the range of 1 to 60 days in the environment.

The term "heteroatom" as used herein means an atom of any element other than carbon or hydrogen. Preferred heteroatoms are nitrogen, oxygen, sulfur and phosphorous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms ortho, meta and para apply to 1,2-, 1,3- and 1,4-disubstituted benzenes, respectively. For example, the names 1,2-dimethylbenzene and ortho-dimethylbenzene are synonymous.

A "phosphoryl" can in general be represented by the formula:

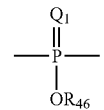

wherein $Q_1$ represents S or O, and $R_{46}$ represents hydrogen, a lower alkyl or an aryl. When used to substitute, e.g., an alkyl, the phosphoryl group of the phosphorylalkyl can be represented by the general formula:

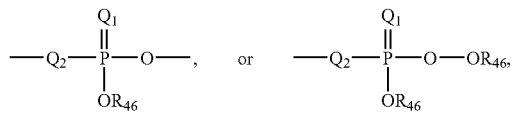

wherein $Q_1$ represents S or O, and each $R_{46}$ independently represents hydrogen, a lower alkyl or an aryl, $Q_2$ represents O, S or N. When $Q_1$ is an S, the phosphoryl moiety is a "phosphorothioate".

"Plant" as used herein refers to any member of the plant kingdom, at any stage of its life cycle, including seeds, germinated seeds, seedlings, or mature plants.

"Plant cell" refers to a cell from a plant or plant component.

"Plant component" refers to a portion or part of a plant. Examples include: seeds, roots, stems, vascular systems, fruits (further including pip fruits (e.g. apples, pears, quinces)), citrus fruits (oranges, lemons, limes, grapefruits, mandarins, nectarines), stone fruits (peaches apricots, plums, cherries, avocados, grapes), berries (strawberries, blueberries, raspberries, blackberries)), leaves, grains and vegetables.

A "plant pathogen" refers to an organism (bacteria, virus, protist, algae or fungi) that infects plants or plant components. Examples include molds, fungi and rot that typically use spores to infect plants or plant components (e.g fruits, vegetables, grains, stems, roots). Spores must recognize the host, attach, germinate, penetrate host tissues, and proliferate hyphae that will allow the fungus access to nutrients for growth and reproduction. Examples include: *Botrytis* sp. (*B. cinerea*), *Penicillium* sp. (*P. expansum, P. italicum, P. digitalum*), *Rhizopus* sp. (*R. sulonifer, R. nigricans*), *Alternaria* sp. (*A. alternata, A. solani*), *Diploidia* sp. (*Diploidia natalenses*), *Monilinia* sp. (*M. fructicola*), *Pseudomonas* sp. (*P. cepacia*) *Xanthomonas* sp., *Erwinia* sp. and *Corynebacte-* rium. *Cladosporium* sp. (*C. fulva*), *Phytophtora* sp. (*P. infestans*), *Colletotricum* spp. (*C. coccoides C. fragariae, C. gloesporioides*), *Fusarium* spp. (*F. lycopersici*), *Verticillium* spp. (*V. alboatrum, V. dahliae*), *Unicula* spp. (*U. necator*), *Plasmopara* spp. (*P. viticola*), *Guignardia* spp. (*G. bidwellii*), *Cercospora* spp. (*C. arachidicola*), *Scelrotinia* spp. (*S. scerotiorum*), *Puccinia* spp. (*P. arachidis*), *Aspergillus* spp. (*A. flavus*), *Venturia* spp (*V. inaequalis,*) *Podosphaera* spp. (*P. leucotricha*), *Pythiun* spp., *Sphaerotheca* (*S. macularis*) and *Bacillus* spp. (*B. subitlis*).

A "polar, aprotic solvent" means a polar solvent as defined above which has no available hydrogens to exchange with the compounds of this invention during reaction, for example DMF, acetonitrile, diglyme, DMSO, or THF.

A "polar solvent" means a solvent which has a dielectric constant ($\epsilon$) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred solvents are DMF, DME, NMP, and acetonitrile.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

"Release rate" or "flux" refers to the rate of delivery or diffusion of a compound to and ultimately from a surface. The release rate may be constant or sustained over a period of time or may be variable. However, constant, controlled or sustained release rates are generally preferred. Steady state or sustained release may be effected by use of a reservoir membrane (i.e. a two layer coating in which one layer contains the active agent and the other creates a membrane through which the active agent can be released). The active agent could alternatively be microencapsulated within any of a variety of matrices for sustained release. Preferred release rates in the range of about 100 to about 200 µgcm$^{-2}$d$^{-1}$ are useful for temporary uses or uses that require reapplication. For more sustained applications, preferred release rates are in the range of about 1 to about 100 µgcm$^{-2}$ d$^{-1}$, more preferably in the range of about 1–50 and still more preferably in the range of about 1–25 or better yet, 1–15.

The term "soluble" refers to the ability to be loosened or dissolved. A "solubilized" compound has been loosened or dissolved (e.g. into a fluid).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfate" is art recognized and includes a moiety that can be represented by the general formula:

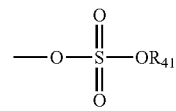

in which $R_4$ is as defined below.

A "sulfate binding moiety" refers to a moiety that is capable of binding or otherwise associating with a sulfate or sulfonate group.

The term "sulfonate" is art recognized and includes a moiety that can be represented by the general formula:

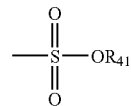

in which $R_{41}$ is an electron pair, hydrogen, alkyl, cycloalkyl, or aryl.

The terms "sulfoxido" or "sulfinyl", as used herein, refers to a moiety that can be represented by the general formula:

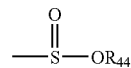

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "surface" as used herein, refers to any interface between an object and a fluid environment, which permits at least intermittent contact between the object and the fluid environment. Fluids contacting the surfaces can be stagnant or flowing, and can flow intermittently or continuously, with laminar or turbulent or mixed rheologies. A surface upon which a biofilm can form can be dry at times with sporadic fluid contact, or can have any degree of fluid exposure including total immersion. Fluid contact with the surface can take place via aerosols or other means for air-borne fluid transmission.

"Sustained release" or "controlled release" refers to a relatively constant or prolonged release of a compound of the invention from a surface. This can be accomplished through the use of diffusional systems, including reservoir devices in which a core of a compound of the invention is surrounded by a porous membrane or layer, and also matrix devices in which the compound is distributed throughout an inert matrix. Microencapsulation techniques can also be used to maintain a sustained focal release of a compound of the invention. Microencapsulation may also be used for providing improved stability. The encapsulated product can take the form of for example, spheres, aggregates of core material embedded in a continuum of wall material, or capillary designs. The core material of a microcapsule containing a compound of the invention may be in the form of a liquid droplet, an emulsion, a suspension of solids, a solid particle, or a crystal. The skilled artisan will be aware of numerous materials suitable for use as microcapsule coating materials, including, but not limited to, organic polymers, hydrocolloids, lipids, fats, carbohydrates, waxes, metals, and inorganic oxides. Silicone polymers are the most preferred microcapsule coating material for treatment of surfaces. Microencapsulation techniques are well known in the art and are described in the Encyclopedia of Polymer Science and Engineering, Vol. 9, pp. 724 et seq. (1989) hereby incorporated by reference.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compositions of the Invention

In certain embodiments, the compositions of the present invention comprise an anti-fouling compound represented by general structure 1:

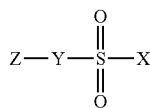

wherein

X represents —OH, —O(aryl), —O(acyl), —O(sulfonyl), —CN, F, Cl, or Br;

Y represents O, S, Se, or NR;

Z represents optionally substituted alkyl, heteroalkyl, cycloalkyl, heterocycloalkyl, aryl, heteroaryl, aralkyl, heteroaralkyl, or —(CH$_2$)$_m$—R$_{80}$;

R represents independently for each occurrence hydrogen, alkyl, heteroalkyl, aryl, heteroaryl, aralkyl, heteroaralkyl, or —(CH$_2$)$_m$—R$_{80}$;

R$_{80}$ represents independently for each occurrence aryl, cycloalkyl, cycloalkenyl, heterocyclyl, or polycyclyl; and m is an integer in the range 0 to 8 inclusive.

Particularly stable compounds are represented by general structure 1 and the attendant definitions, wherein X represents —OH, F, Cl, or Br.

In other preferred embodiments, the compositions of the present invention comprise an anti-fouling compound represented by general structure 1 and the attendant definitions, wherein Y represents O.

In certain embodiments, the compositions of the present invention comprise an anti-fouling compound represented by general structure 1 and the attendant definitions, wherein Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein Z represents methyl, octyl, 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein R represents H or alkyl.

In certain embodiments, the compositions of the present invention comprise an anti-fouling compound represented by general structure 1 and the attendant definitions, wherein X represents —OH, F, Cl, or Br; and Y represents O.

In certain embodiments, the compositions of the present invention comprise an anti-fouling compound represented by general structure 1 and the attendant definitions, wherein X represents —OH or Cl; and Y represents O.

In certain embodiments, the compositions of the present invention comprise an anti-fouling compound represented by general structure 1 and the attendant definitions, wherein X represents —OH, F, Cl, or Br; and Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein X represents —OH or Cl; and Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein X represents —OH, F, Cl, or Br; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein X represents —OH or Cl; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein X represents —OH, F, Cl, or Br; and Z represents methyl, octyl, 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein X represents —OH or Cl; and Z represents methyl, octyl, 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein Y represents O; and Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein Y represents O; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein Y represents O; and Z represents methyl, octyl, 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein X represents —OH, F, Cl, or Br; Y represents O; and Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein X represents —OH or Cl; Y represents O; and Z represents optionally substituted alkyl, aryl, or —(CH$_2$)$_m$—R$_{80}$.

In certain embodiments, the compositions of the present invention comprise an anti-fouling compound represented by general structure 1 and the attendant definitions, wherein X represents —OH, F, Cl, or Br; Y represents O; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein X represents —OH or Cl; Y represents O; and Z represents optionally substituted alkylphenyl, heteroalkylphenyl, arylphenyl, or heteroarylphenyl.

In certain embodiments, the compositions of the present invention comprise an anti-fouling compound represented by general structure 1 and the attendant definitions, wherein X represents —OH, F, Cl, or Br; Y represents O; and Z represents methyl, octyl, 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

In certain embodiments, the compositions of the present invention comprise an anti-fouling compound represented by general structure 1 and the attendant definitions, wherein X represents —OH or Cl; Y represents O; and Z represents methyl, octyl, 4-(2-methylpropyl)phenyl, 4-(1,1-dimethylethyl)phenyl, 4-(1,1-dimethylpropyl)phenyl, 4-pentylphenyl, 4-(1-methyl-1-phenylethyl)phenyl, or 4-(1-methylheptyl)phenyl.

One of skill in the art will recognize that the composition of the invention can be varied as required to optimize the overall chemical properties of the particular compound for specific uses, while retaining the activity. For example, the length of an alkyl chain can be extended or shortened to control the rate of dissolution of the compound from a structure or a coating. Alternatively, additional functional groups can be added to the alkyl chain to further vary the chemical nature of the molecule.

The present invention is further illustrated by the following examples, which should not be construed as limiting in any way. The contents of all cited references including literature references, issued patents and published patent applications as cited throughout this patent application are hereby expressly incorporated by reference.

EXAMPLES

Example 1

Inhibition of Surface Attachment of *C. fragariae* by Zosteric Acid

In vitro evaluation of zosteric acid for disease control efficacy indicated that the sodium salt of zosteric acid was an effective non-toxic fimgal control agent for Strawberry (cv. Chandler-susceptible variety) anthracnose caused by *Colletotrichum fragariae*. Detached leaf and petiole assays were employed to determine an effective dose. An optimum effective concentration of about 2% (which is within a range that is commercially viable) was obtained when the agent was applied in phosphate buffer (pH 7.0) containing 0.1% Tween 20, and when plant tissues were sprayed to wetness with a spore density of $1.5\times10^6$ spores/mL (FIG. 1).

Greenhouse evaluations of zosteric acid for efficacy in control of anthracnose crown rot of strawberry confirmed that the optimal concentration of zosteric acid was 2% for *C. fragariae*. It was found that the disodium salt of zosteric acid showed very low or no detectable phytotoxicity.

Spore attachment assays ascertained that the most effective analogs, where the sodium salt of zosteric acid and the TPPC analog (FIG. 3). The 1% zosteric acid prevented spores from germinating during the 24 hour incubation while the lower concentrations (0.1 and 0.01%) reduced the number of spores germinating (FIG. 4). Post-harvest treatment of ripe blueberries with zosteric acid sodium salt and a zosteric acid analog followed by innoculation with *C. acutatum* resulted in a decrease of about 50% in the number of infected berries in the 0.67 and 2% zosteric acid analog treatment.

Example 2

Inhibition of Surface Attachment of Marine Bacteria by Alkyl Sulfates

Octyl sulfate is an alkyl sulfate surfactant with extensive industrial applications, and is manufactured by several large chemical companies. To investigate potential AF properties of the sulfate ester octyl sulfate, it was incorporated into an inert coating material that was then coated onto a surface to be exposed to conditions that support the formation of marine algal biofilms.

Materials and Methods

Figure 5:
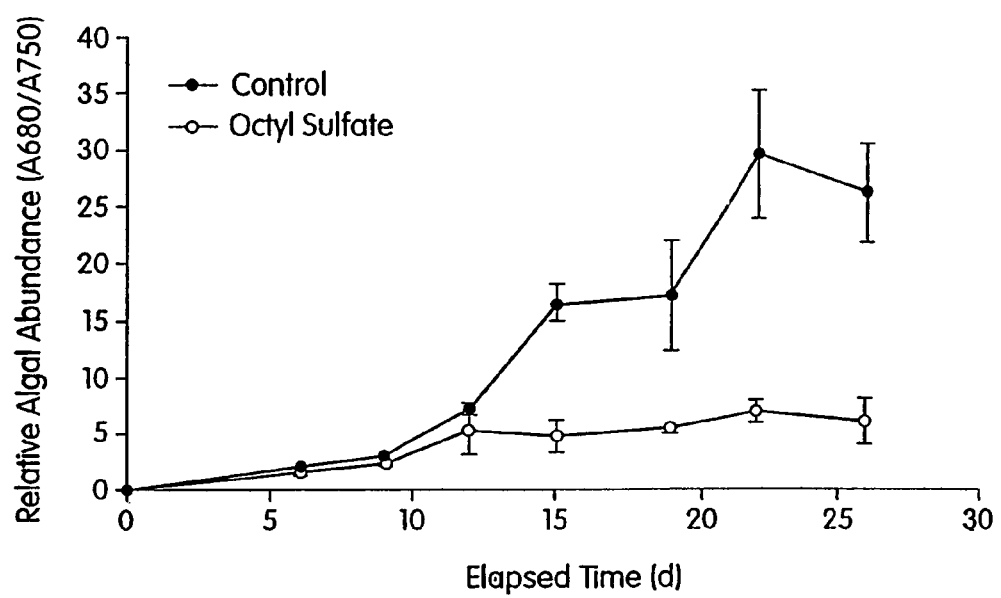
FIG. 5 is a diagrammatic representation of the results of marine algae attachment assays measuring the abundance of algal biofilm development on the inert coating RTV-11 compared to biofilm development on RTV-11 with octyl sulfate incorporated into the coating. Relative algal abundance represents the attachment of the marine algae to the tested surface. Error bars indicate 1 standard error of the mean (n=3) for each treatment. The ratio of the optical densities measured at wavelengths 680 nm and 750 nm ($A_{680}/A_{750}$) at time O was used as a baseline reference for all samples.

A 30% (w/v) solution of octyl sulfate in water (Stepan Chemical Co.) was evaporated to dryness under a stream of room temperature air, to recover pure octyl sulfate (FIG. 5). The dry octyl sulfate was incorporated into RTV-11 silicone polymer at a loading of 25% (wt/wt) (RTV-11 silicone, catalyst and primer obtained from General Electric). The mixture was applied to three glass slides previously primed with silicone primer, and allowed to cure to dryness. Three primed glass slides coated with pure RTV-11 served as agent-free controls. After complete drying, the absorption properties of each slide were measured using a Shimadzu UV-2101 spectrophotometer fitted with an integrating sphere. Slides were then placed in a tank of running raw seawater and allowed to incubate outdoors in natural sunlight for 26 days. Water temperature was nominally 15 C. Spectrophotometric determination of biofilm accumulation was measured on each slide periodically. Relative algal biomass was calculated as the ratio of absorption at 680 nm, contributed by chlorophyll α, to that at 750 nm, a wavelength not absorbed by chlorophyll, to correct for differences in turbidity and scattering properties of the different slides.

Results

As shown in FIG. 5, octyl sulfate incorporated into RTV-11 silicone, and then coated onto glass slides, significantly inhibited the formation of natural marine algal biofilms in natural seawater. After 26 days of incubation in running seawater, algal biofilm development on the octyl sulfate containing coatings was five fold less than that of controls lacking octyl sulfate, indicating that octyl sulfate possesses strong AF activity.

Studies were performed to evaluate the ability of the sulfate ester molecules octyl sulfate and methyl sulfate, to inhibit adhesion of the marine bacteriums *Oceanosprillum* and *Alteromonas atlantica* to glass surfaces.

Materials and Methods

*Oceanosprillum* adhesion test Each test consisted of a control set (with no sulfate esters) and sample sets containing the test molecules. The first test group consisted of a control sample set, a zosteric acid (5 mM) sample set, and an octyl sulfate (5 mM) sample set. The second test group consisted of a control sample set, a zosteric acid (5 mM) sample set, and a methyl sulfate (5 mM) sample set. Sample sets consisted of five 50 mL sterile centrifuge tubes, with each tube containing a glass microscope slide, 50 ml of artificial seawater (ASTM—American Society for testing and materials) with the dissolved sulfate ester, inoculated with an *Oceanosprillum* culture at 1×10$^6$ cells/mL. Sample sets were incubated at 23 C, with shaking so that the surface of the slides were horizontal. Over a 6-hour period, individual tubes were taken from the sample sets and tested for microbial adhesion.

*Alteromonas atlantica* adhesion tests. The tests consisted of a control sample set, a zosteric acid (5 mM) sample set, an octyl sulfate (5 mM) sample set, and a methyl sulfate (5 mM) set. A sample set consisted of six 60 mL sterile centrifuge tubes. Each tube contained a glass microscope slide and 50 mL of modified ASTM seawater (American Society for Testing and Materials (1986) D1141-86, ASTM, Philadelphia, Pa.) with dissolved agent, inoculated with *Alteromonas atlantica* culture to an initial cell density of 1×10$^6$ cells/mL. The modified seawater consisted of normal ASTM seawater ingredients, however the carbon source glycerol, was only 1000th the normal strength, 0.1 L/L instead of 100 L/L, and was void of an amino acid source (casamino acids), in order to allow enough carbon for attachment, but not for significant cell growth.

Determination of bacterial adhesion. Samples were removed from the shaker and 1 mL of 50× acridine orange stain (0.5 g/L acridine powder in water) was added to the tube. The stain was allowed to react for 4 minutes. The slides were then removed and fitted with a long cover slip and immediately counted with an epifluorescent microscope fitted with a 100× (oil) objective lens on the under side of the slide. The size of the counting field was 10×10 μm. A total of 20 counts per slide were performed and averaged to yield the number of cells per μm$^2$, which was in turn converted to cells per mm$^2$. Error was assigned at 10% which is the standard accepted error for direct counting of bacterial cells.

Results

Figure 4:
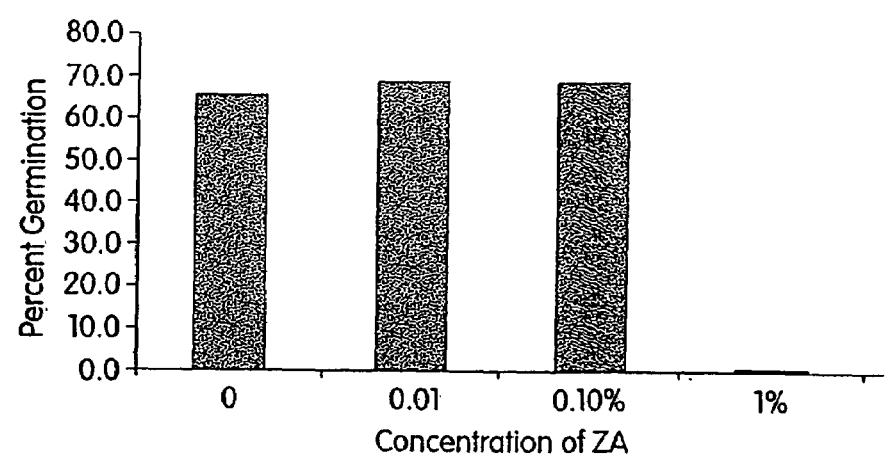
FIG. 4 is a graph showing the results of microscopic evaluation of *C. acutatum* spores. As can be seen in the graph. 1% zosteric acid prevented 99% of the spores from germinating during the 24 hour incubation.
Figure 6:
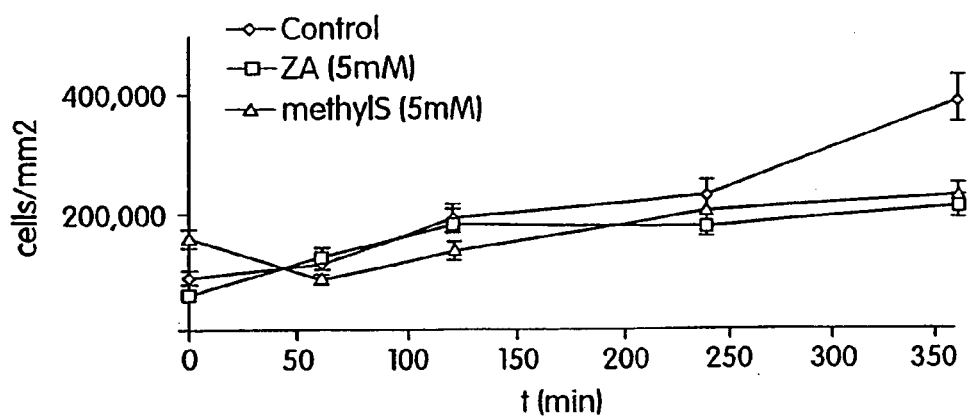
FIG. 6 is a diagrammatic representation of the results of bacterial attachment assays performed with the marine bacterium *Oceanosprillum*, cultured in the presence and absence of either zosteric acid or methyl sulfate.
Figure 7:
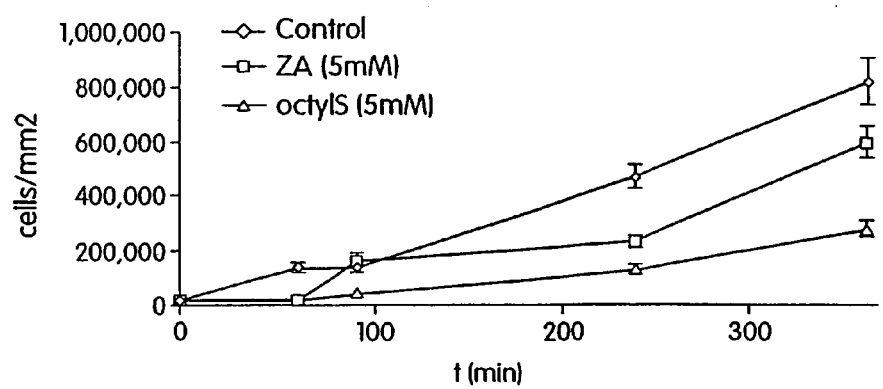
FIG. 7 is a diagrammatic representation of the results of bacterial attachment assays performed with the marine bacterium *Oceanosprillum*, cultured in the presence and absence of either zosteric acid or octyl sulfate.

As shown in FIG. 6, the presence of octyl sulfate or methyl sulfate in the medium significantly reduced bacterial adhesion to the glass slides when compared to controls in which no sulfate ester molecule was present. Methyl sulfate inhibited *Oceanosprillum* adhesion to an extent similar to the proven AF agent zosteric acid, with each compound promoting roughly a two fold reduction in bacterial attachment, relative to control. As shown in FIG. 4, octyl sulfate inhibited *Oceanosprillum* adhesion to an even greater extent than zosteric acid.

Figure 8:
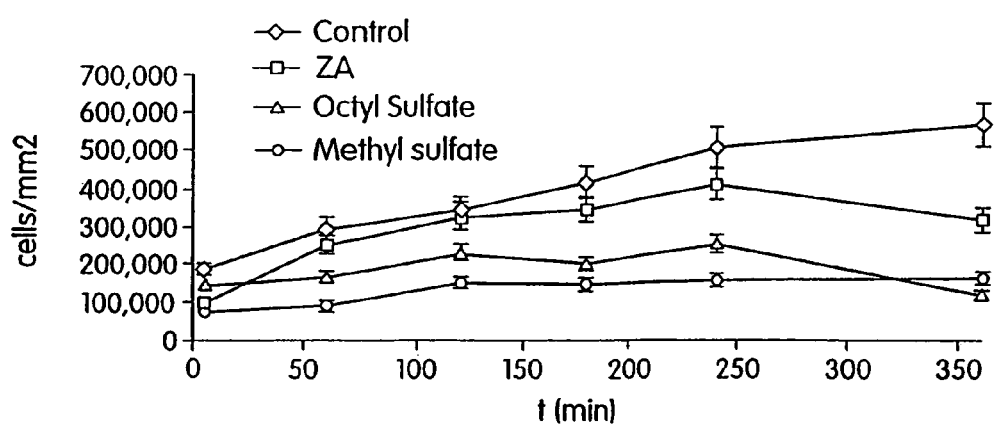
FIG. 8 is a diagrammatic representation of the results of bacterial attachment assays performed with the bacterium *Alteromonas atlantica*, performed in the presence and absence of either, zosteric acid, octyl sulfate, or methyl sulfate.

As shown in FIG. 8, the presence of dissolved zosteric acid, octyl sulfate, or methyl sulfate produced a significant reduction in the marine bacterium, *Alteromonas atlantica* adhesion relative the controls. The presence of methyl sulfate had the most dramatic effect upon adhesion, with adhesion remaining constant after 120 minutes at 150,000 cells/mm$^2$, while controls had greater than 700,000 cells/mm$^2$. Octyl sulfate also inhibited adhesion, demonstrating a slightly higher inhibitory activity than zosteric acid.

Example 3

Inhibition of Fungal Surface Attachment and Mycelial Development

To determine the effectiveness of sulfate esters at inhibiting fungal biofouling, the ability of zosteric acid to inhibit attachment of the fungus *Aureobasidium pullulans* to surfaces was examined.

Materials and Methods

*Aureobasidium pullulans* (ATCC 34261) was grown on potato-dextrose agar and harvested according to ASTM G-21-90 protocols (American Society for Testing and Materials (1986) D1141-86, ASTM, Philadelphia, Pa.). The resulting spore suspension was used to inoculate liquid culture tubes containing 35 mL of growth medium (nutrient salts with 5 mM sucrose) and 15 mM zosteric acid. Zosteric acid-free medium was prepared as a control. A sterile microscope slide was added to each tube, the tubes were sealed and placed on a rotary shaker table at room temperature. One tube was harvested each day by removing the slide and counting the number of attached spores by direct microscopic counts, as described above.

Results

Figure 9:
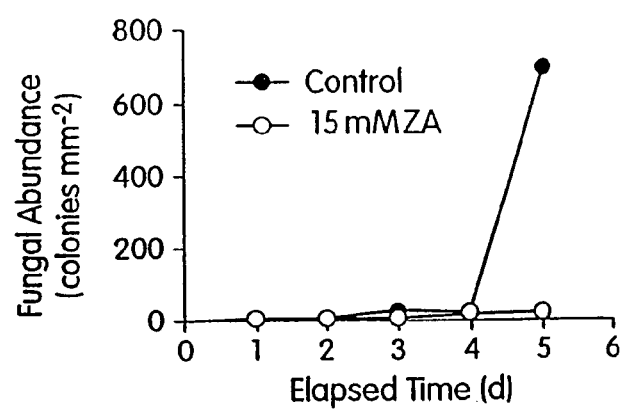
FIG. 9 is a diagrammatic representation of the results of fungal attachment and growth assays using the fungus *Aureobasidium pullulans* (a shower fungus that stains grout) grown in the presence and absence of zosteric acid, where fungal abundance represents the attachment of *A. pullulans* to the exposed surface.

Fungal spores were observed to grow in both the presence and absence of zosteric acid, as indicated by the clouding of all tubes after Day 1. However, as shown in FIG. 9, the presence of zosteric acid prevented the attachment of the fungus to the glass slides. After 5 days incubation with *A. pullalans*, less than 20 germinated fungal colonies/mm$^2$ were observed on slides incubated in the additional presence of zosteric acid, compared to more than 600 germinated fungal colonies/mm$^2$ on control slides. Furthermore, fungal colonies in the media of zosteric acid free cultures were composed of multi-cellular (>20 cells) filaments, indicative of mycelial growth. In contrast, colonies in the zosteric acid treated cultures were generally small and round, exhibiting no evidence of filamentous growth or mycelial development.

Example 4

Sulfate Esters Bind Cell Surfaces of *Shewanella putrefaciens*

To investigate the mechanism behind the AF activity of sulfate esters, polyclonal antibodies specific for the sulfate ester zosteric acid were generated (BAbCo, Berkeley, Calif.). Preliminary testing of these antibodies for cross reactivity towards related compounds lacking the sulfate ester group (cinnamic acid, ferulic acid, coumaric acid) showed no cross reactivity, suggesting that the specific domain recognized by the antibodies probably includes the sulfate ester group. These antibodies were then used to investigate whether the sulfate ester AF agent zosteric acid directly binds fouling organisms.

The marine bacterium *Shewanella putrefaciens* were grown in cultures containing zosteric acid and were subsequently examined for bound zosteric acid using immuno-gold staining with the antibody described above. Electron microscopic examination of immunoprobed *S. putrefaciens* detected zosteric acid molecules bound to the surface of the bacteria. Furthermore, zosteric acid was observed to be present at high incidence at the sites of cell adhesion. In contrast to these agglutination sites, the majority of the cell surfaces as well as the continuous boundaries between daughter cells in dividing chains, showed no evidence of bound zosteric acid, as indicated by a lack of immuno-gold staining. These results indicate that sulfate esters bind to the surfaces of bacterial cells and suggest a possible relationship between sulfate ester binding sites and the sites of bacterial agglutination.

Example 5

Zosteric Acid Promotes Bacterial Agglutination

To further investigate the role of sulfate esters in agglutination, the ability of sulfate esters to facilitate the agglutination of bacterial cells was investigated. Log-phase cultures grown in the presence of zosteric acid were monitored spectrophotometrically ($OD_{600}$) for growth, and for agglutination in the presence of increasing amounts of zosteric acid.

Materials and Methods

Cell Surface Binding Assays. The marine bacterium *Shewanella putrefaciens* was grown in marine broth in the presence of 16 mM zosteric acid. Dense log phase cells were harvest after 5 hours growth, and preserved in 0.5× Kamofsky's fixative (2% formaldehyde, 2.5% gluturaldehyde, 0.05 M sodium cacodylate, 0.25 M sucrose, pH 7.4) for 2 hours, and then transferred to a cacodylate buffer (0.05 M sodium cacodylate, pH 7.4) for storage. Cells were prepared for electron microscopic examination using immuno-gold staining techniques (Harlow, E. and Laine, D., Antibodies, A Laboratory Manual, Cold Spring Harbor Laboratory, 359–421; Roth et al., *J. Histochem. Cytochem.* 26: 1074–1081 (1978)). The primary antibody used in this study was an anti-zosteric acid polyclonal antibody (BAbCo, Richmond, Calif.).

Bacterial agglutination assays. Log-phase cultures of *Shewanella putrefaciens* were grown in complete seawater medium containing zosteric acid at a range of concentrations up to 20 mM. Cultures were counted for viable colony forming units at eight hours.

Results

Figure 10:
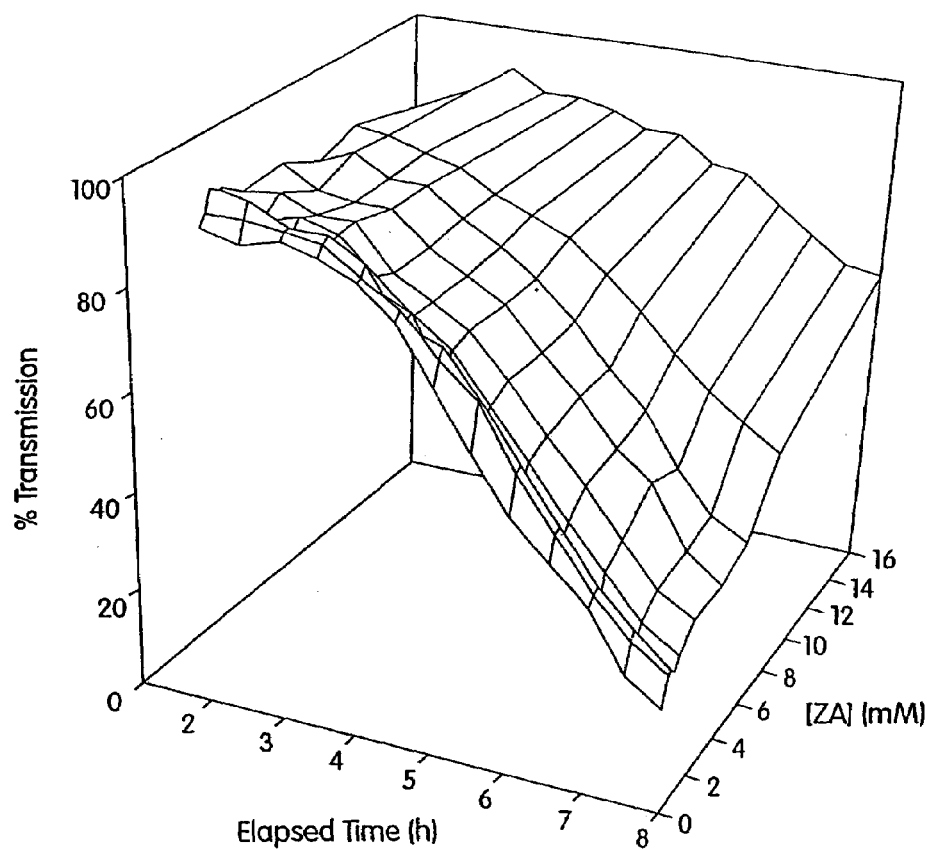
FIG. 10 is a diagrammatic representation of the results of agglutination of the bacterium *Shewanella putrefaciens* induced by the presence of increased amounts of zosteric acid, measured by the percent transmission (% T) of the liquid cultures at wavelength 600 nm. Agglutination is indicated by the concentration-dependent increase in % T of cultures grown in the presence of zosteric acid. In this case, relatively high levels of % T exhibited by the zosteric acid-exposed cultures do not reflect differences in growth, as counts of viable colony forming units exhibited no difference in cell density at eight hours.

Although zosteric acid concentrations up to 16 mM did not inhibit the growth of *S. putrefaciens* in liquid culture, the presence of zosteric acid caused significant agglutination of *S. putrefaciens* in a concentration dependent manner. The agglutination observed was visible to the naked eye, and was more quantitatively detected as a decrease in optical density absorbance in cultures containing zosteric acid (FIG. 10). Counts of viable colony forming units at eight hours revealed no difference in cell density among the different cultures, thus the observed differences in absorption resulted from differences in bacterial agglutination, not differences in growth (cell division) rates among the cultures.

Equivalents

Those skilled in the art will recognize, or be able to ascertain using no more than routine experimentation, many equivalents of the specific embodiments of the invention described herein. Such equivalents are encompassed by the following claims.

The invention claimed is:

1. A coating for contacting a plant surface comprising an effective amount of a compound represented by general structure 2:

2

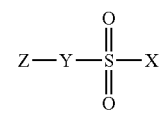

wherein

X represents —OH, F, Cl, or Br:

Y represents O;

Z represents optionally substituted alkylphenyl, or $-(CH_2)_m-R_{80}$, wherein when Z is substituted, a substituent is selected independently for each occurrence from the group consisting of alkyl and aralkyl;

$R_{80}$ represents independently for each occurrence aryl; and m is an integer in the range of 0 to 8 inclusive;

wherein the coating releases the compound or a biologically active fragment thereof, and wherein the compound is microencapsulated with a microcapsule coating material comprising an organic polymer, hydrocolloids, lipid, fat, carbohydrate, wax, inorganic oxide, or silicone polymer.

2. The coating of claim 1, wherein Z represents optionally substituted alkylphenyl or aralkylphenyl.

3. The coating of claim 1, wherein Z represents 4-(2-methylpropyl)phenyl, 4-(1,1-dimethyethyl)phenyl, 4-(1,1-dimethylpropyl)phenyl, 4-pentylphenyl, 4-(1-methyl-1-phenylethyl)phenyl, or 4-(1-methylheptyl)phenyl.

4. The coating of claim 1, wherein the coating comprises water.

5. The coating of claim 1, wherein the coating comprises an inorganic oxide.

6. The coating of claim 1, wherein the coating comprises a silicone polymer.

* * * * *